(12) United States Patent
Blatter et al.

(10) Patent No.: US 9,458,146 B2
(45) Date of Patent: Oct. 4, 2016

(54) CRYSTALLINE SODIUM SALT OF AN HIV INTEGRASE INHIBITOR

(75) Inventors: Frtiz Blatter, Reinach (CH); Katharina Reichenbächer, Rheinfelden (DE); Robert Ziegert, Munster (AT); Josef Wieser, Kundl (AT); Johannes Ludescher, Breitenbach (AT)

(73) Assignee: SANDOZ AG, Basel (CH)

( * ) Notice: Subject to any disclaimer, the term of this patent is extended or adjusted under 35 U.S.C. 154(b) by 68 days.

(21) Appl. No.: 14/115,316

(22) PCT Filed: Apr. 27, 2012

(86) PCT No.: PCT/EP2012/057712
§ 371 (c)(1),
(2), (4) Date: Feb. 3, 2014

(87) PCT Pub. No.: WO2012/150183
PCT Pub. Date: Nov. 8, 2012

(65) Prior Publication Data
US 2014/0135353 A1 May 15, 2014

(30) Foreign Application Priority Data
May 3, 2011 (EP) .................................... 11164530

(51) Int. Cl.
*A61K 31/505* (2006.01)
*C07D 413/12* (2006.01)

(52) U.S. Cl.
CPC .................... *C07D 413/12* (2013.01)

(58) Field of Classification Search
CPC ........................... C07D 413/12; A61K 31/505

USPC .......................................... 514/269; 544/319
See application file for complete search history.

(56) References Cited

U.S. PATENT DOCUMENTS 7,169,780 B2 * 1/2007 Crescenzi .......... C07D 239/557
514/235.8

FOREIGN PATENT DOCUMENTS

WO    WO 2006/060730 A2    6/2006

OTHER PUBLICATIONS

International Search Report issued in PCT/EP2012/057712, mailed Jul. 11, 2012, 2 pages.

* cited by examiner

*Primary Examiner* — James O Wilson
*Assistant Examiner* — Ebenezer O Sackey
(74) *Attorney, Agent, or Firm* — Arent Fox LLP

(57) ABSTRACT

A crystalline sodium salt of a compound of formula I (INN: Raltegravir)

Figure 1:
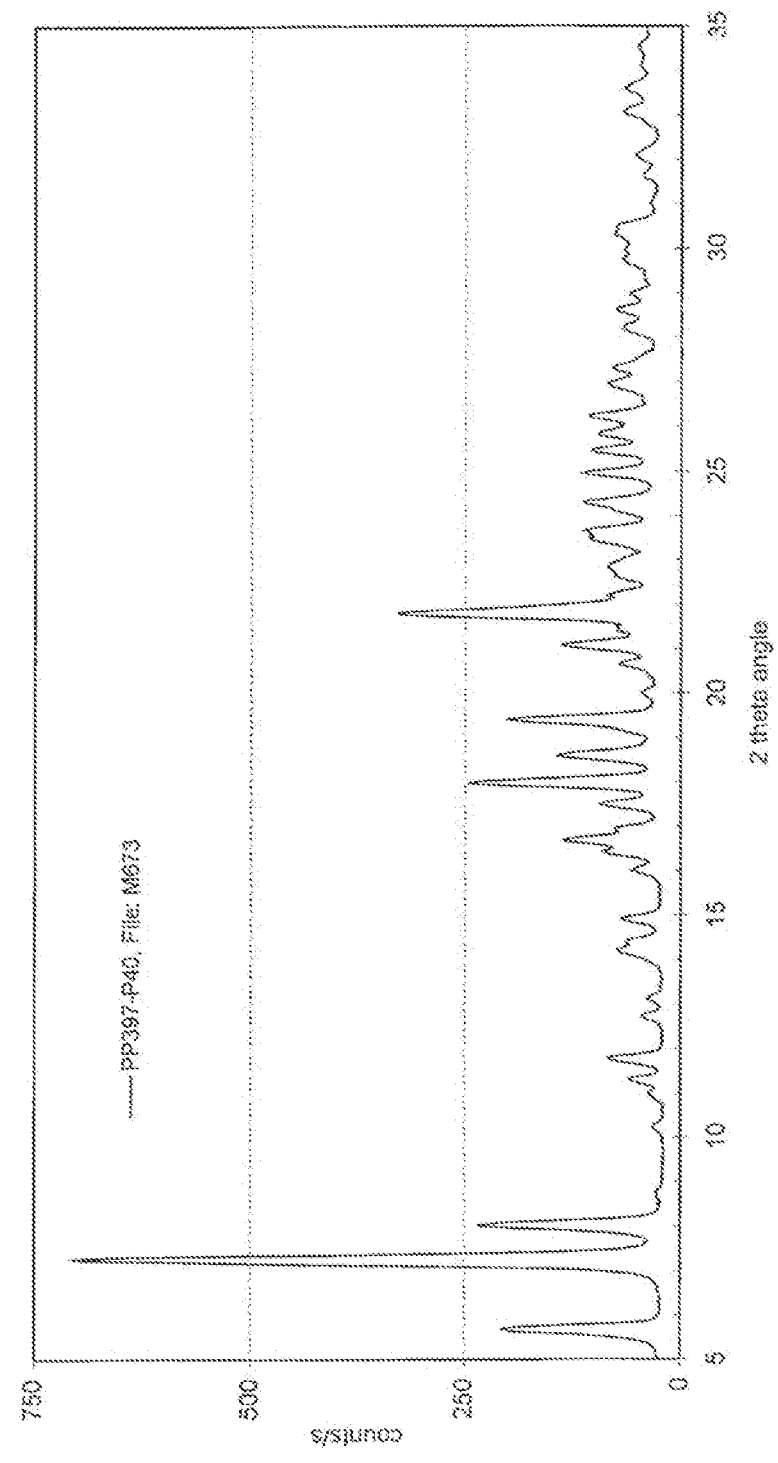

formula I or a hydrate/solvate thereof is disclosed as well as a process for obtaining the same.

25 Claims, 11 Drawing Sheets

FT-Raman spectrum of form B

FT-Raman spectrum of form C

XRPD pattern of form D

XRPD pattern of form E

XRPD pattern of form F

XRPD pattern of form G

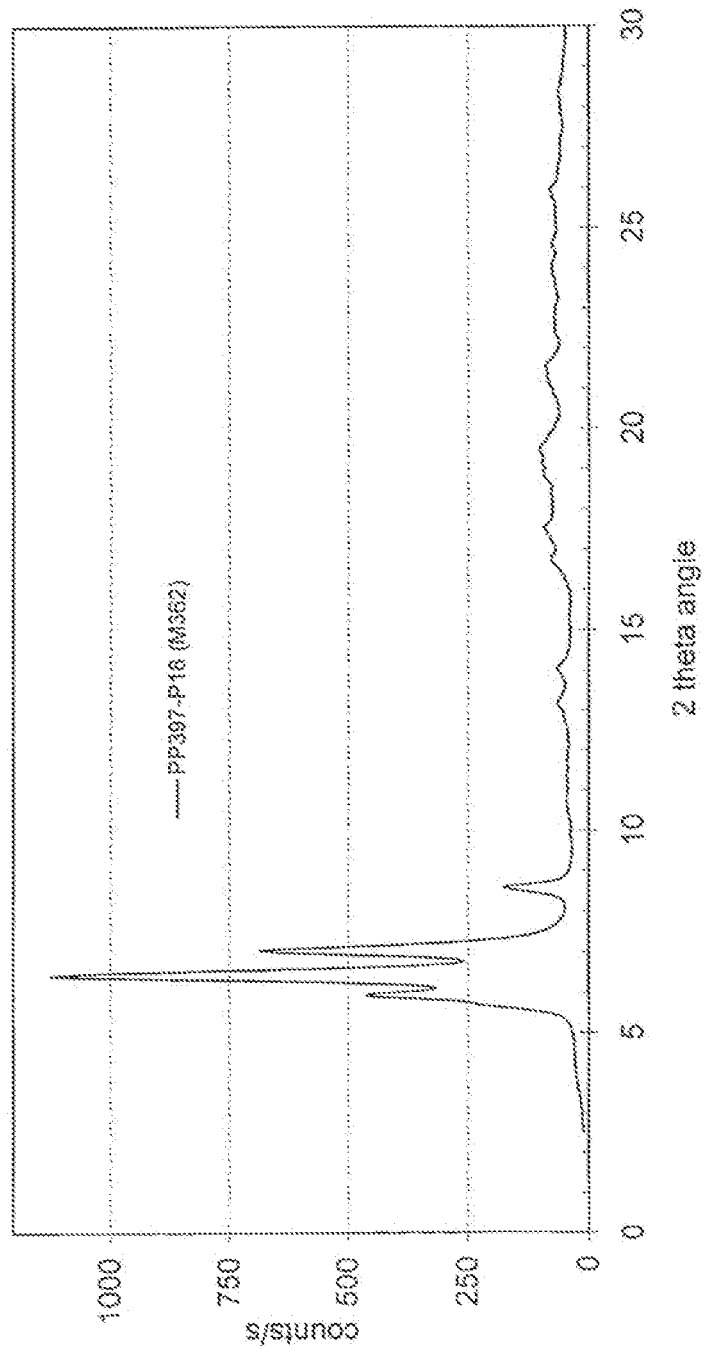

CRYSTALLINE SODIUM SALT OF AN HIV INTEGRASE INHIBITOR

CROSS-REFERENCE TO RELATED APPLICATION

This application is a National Stage entry of International Application No. PCT/EP2012/057712, filed Apr. 27, 2012, which claims priority to European Application No. 11164530.5, filed May 3, 2011, the entire specifications, claims and drawings of which are incorporated herewith by reference.

The present invention is directed to a crystalline sodium salt of an HIV integrase inhibitor as well as to a process for obtaining the same.

WO 03/035077 A1 is directed to N-substituted 5-hydroxy-6-oxo-1,6-dihydropyrimidine-4-carboxamides and pharmaceutically acceptable salts thereof, their synthesis, and their use as inhibitors of the HIV integrase enzyme. The compounds and pharmaceutically acceptable salts are useful for preventing or treating infection by HIV and for treating or delaying the onset of AIDS. In said reference numerous compounds are disclosed as being good for preventing or treating an infection by HIV.

However, WO 03/035077 A1 is silent on crystalline salts of the title compound of the present invention (INN: Raltegravir) having formula I

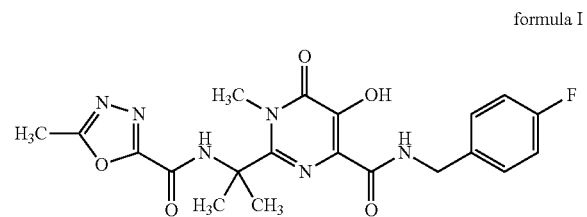 [SMILES: Cc1nnc(C(=O)NC(C)(C)c2nc(C(=O)NCc3ccc(F)cc3)c(O)c(=O)n2C)o1]

formula I

The name of the compound of formula I is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide.

WO 2006/060730 A2 is directed to a potassium salt, particularly a crystalline potassium salt of the compound of formula I. In WO 2006/060730 A2 the potassium salts are described to be significantly more soluble in water compared to the free base. However, WO 2006/060730 A2 does not disclose the solubility of the claimed potassium salt in water.

It is noteworthy that WO 2006/060730 A2 discloses on page 2, lines 10 to 12, that attempts to prepare a crystalline sodium salt of the compound of formula I have been unsuccessful, resulting only in amorphous material. Thus, WO 2006/060730 A2 is silent on a crystalline sodium salt of the compound of formula I. On the contrary, said document teaches that a crystalline sodium salt can not be prepared and is not available to the skilled artisan.

It is therefore an objective of the present invention to provide a novel pharmaceutically acceptable salt of raltegravir with good solubility/dissolution properties. It is also an objective of the present invention to provide raltegravir in a form of a salt having a good chemical and/or physical stability and/or good processability, both during its preparation as an active pharmaceutical ingredient as well as in the preparation of pharmaceutical compositions containing raltegravir. Moreover, the aim of the present invention is the provision of an accurate process for obtaining the salt with high yield and a low complexity. For instance, the loss of the compound of formula I during the conversion into a salt should be reduced.

The present invention provides a crystalline sodium salt of a compound of formula I (INN: Raltegravir)

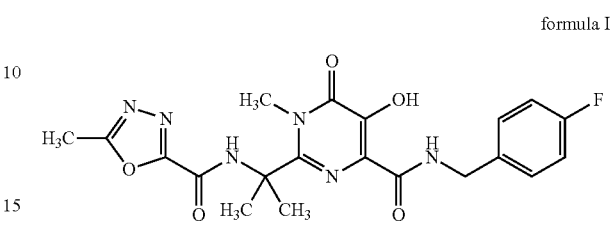

formula I or a hydrate/solvate thereof.

Preferably, the molar ratio of the compound of formula I and sodium is in the range of from 1:0.5 to 1:1.

The crystalline sodium salt of the present invention comprises raltegravir (compound of formula I) and sodium in form of a salt. Raltegravir may be a deprotonated anion, for example raltegravir deprotonated at the nitrogen atom of an amide group and the respective counterion may be a sodium cation. Preferably, as empirical formula the crystalline sodium salt comprises raltegravir anions and sodium cations in the denoted molar ratio.

Moreover, the crystalline sodium salt may contain water. In such cases it is designated as a hydrate. In case the crystalline sodium salt contains a solvent it is designated as a solvate.

The invention also provides processes for forming the crystalline sodium salt of raltegravir and pharmaceutical compositions comprising said crystalline sodium salt of raltegravir.

In the context of the present invention the following abbreviations apply unless explicitly stated otherwise:
 XRPD: Powder X-ray diffraction
 r.h.: relative humidity
 r.t.: room temperature
 DSC: Differential scanning calorimetry
 TG-FTIR: Thermogravimetry coupled with FT-infrared spectroscopy Preferably, the crystalline sodium salt has an XRPD pattern with at least one characteristic peak (expressed in 2θ±0.2° 2θ (CuKα radiation)) at 5.7°, 7.3°, 8.0°, 18.0° and 21.8°, designated as form A. Preferably, form A has an XRPD pattern with at least one characteristic peak (expressed in 2θ±0.2° 2θ (CuKα radiation)) at 5.7°, 7.3°, 8.0°, 11.8°, 16.7°, 18.0°, 18.86, 19.4°, 21.1° and 21.8°. Typically such an X-ray powder diffractogram is measured with copper K-alpha radiation. An X-ray powder diffractogram of a sample of form A is shown in FIG. 1 and the present invention, in a preferred embodiment, relates to form A displaying a XRPD pattern which is substantially in accordance with FIG. 1.

Figure 2:
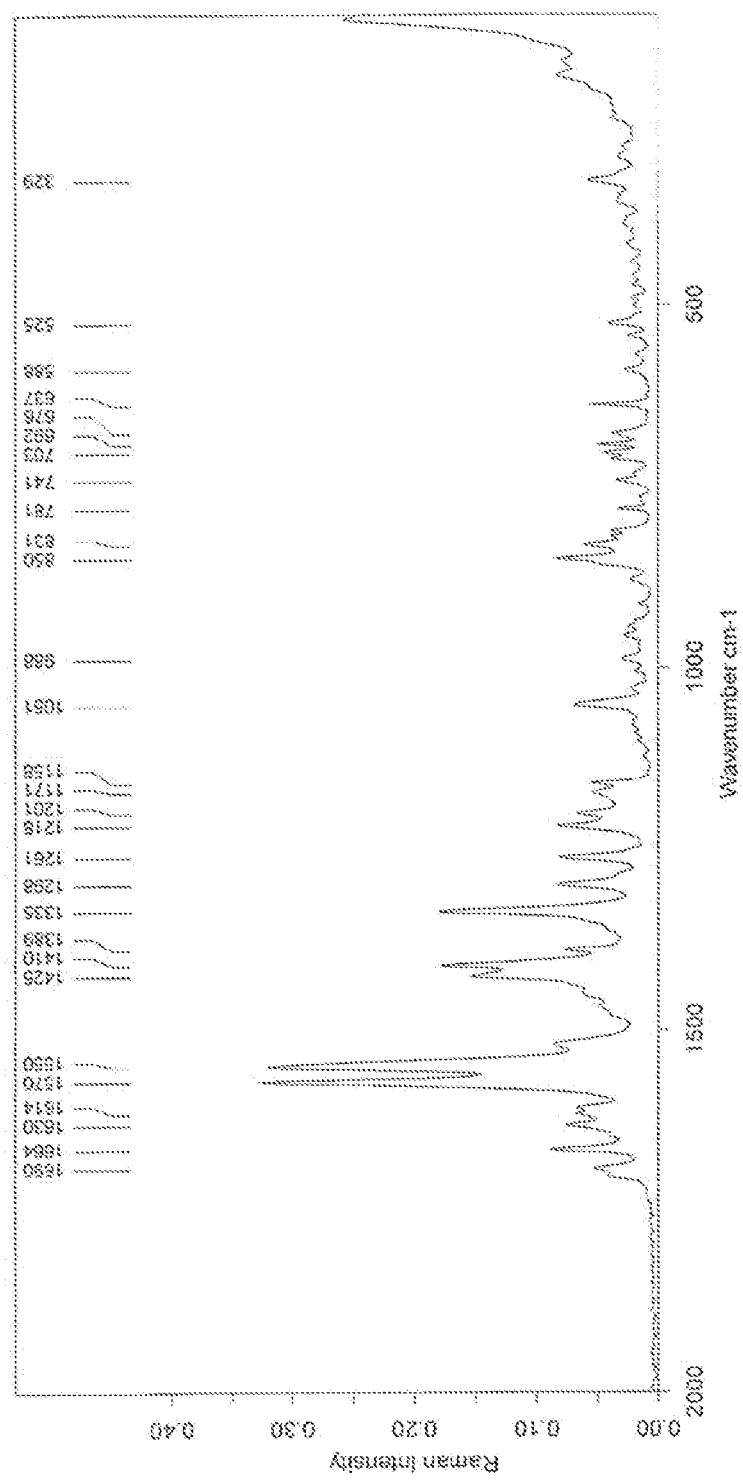

Preferably, form A has a FT-Raman spectrum comprising peaks at wavenumbers (expressed in ±2 cm$^{-1}$) of 637, 692, 850, 1051, 1218, 1261, 1298, 1335, 1410, 1550, 1570, 1630, 1664, 1690, 2937 and 3073 cm$^{-1}$. An FT Raman spectrum of a sample of form A is shown in FIG. 2. In a preferred embodiment, form A is characterized by an FT Raman spectrum substantially in accordance with FIG. 2.

When form A is suspended in water the concentration in the liquid phase is 47±5 mg/ml (22±2° C.) and the pH of the liquid phase is 10.4. Moreover, form A is retained in the suspension. Thus, form A has a good solubility and stability in water. Moreover, form A can be stored at elevated temperature without decomposition. Consequently, form A also has a good thermal stability.

Figure 3:
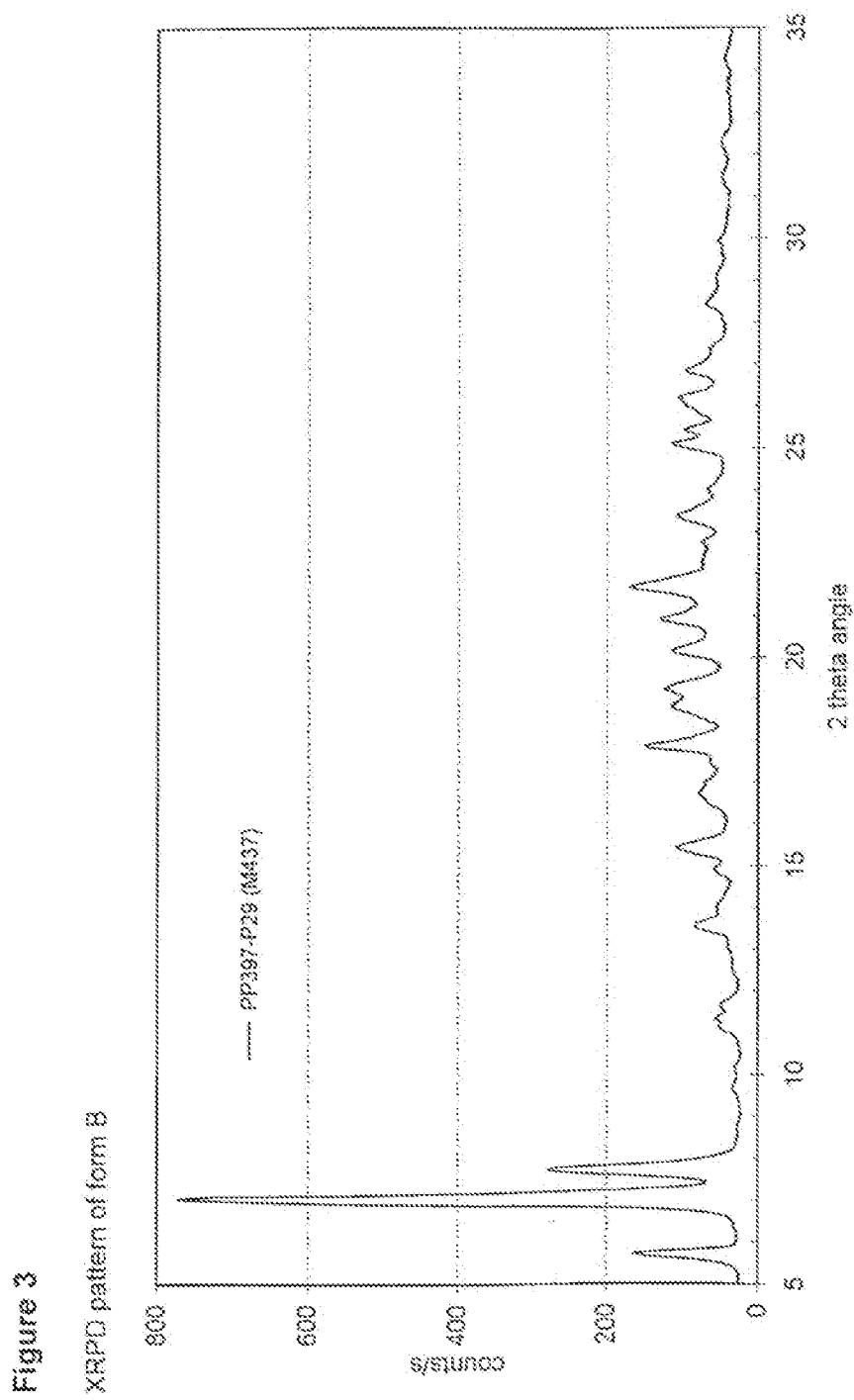

Preferably, the crystalline sodium salt has an XRPD pattern with at least one characteristic peak (expressed in 2θ±0.2° 2θ (CuKα radiation)) at 5.7°, 7.0° and 20.9°, designated as form B. Preferably, form B has an XRPD pattern with at least one characteristic peak (expressed in 2θ±0.2° 2θ (CuKα radiation)) at 5.7°, 7.0°, 7.7°, 15.4°, 17.9°, 20.9° and 21.7°. Typically such an X-ray powder diffractogram is measured with copper K-alpha radiation. An X-ray powder diffractogram of a sample of form B is shown in FIG. 3 and the present invention, in a preferred embodiment, relates to form B displaying a XRPD pattern which is substantially in accordance with FIG. 3.

Figure 4:
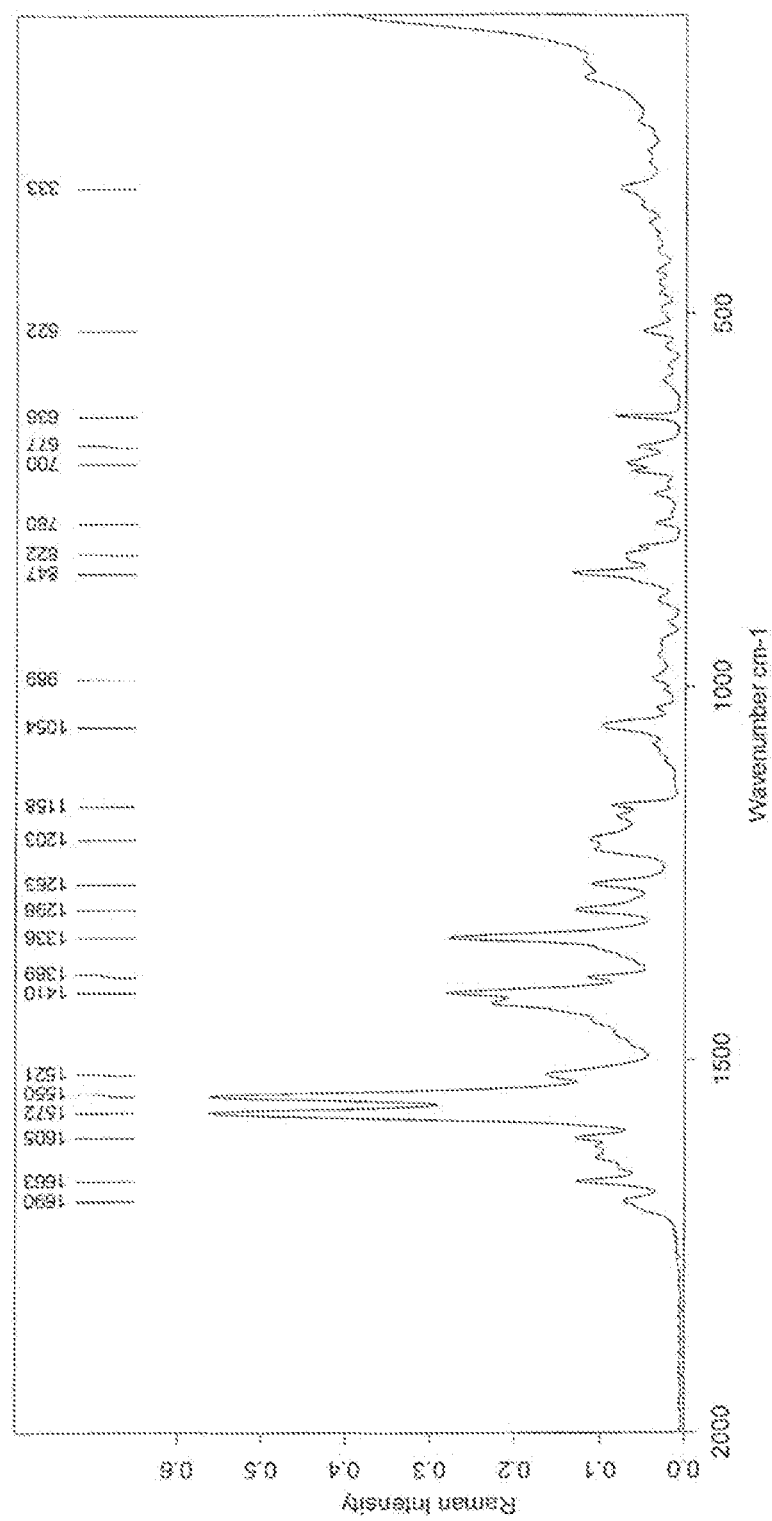

Preferably, form B has a FT-Raman spectrum comprising peaks at wavenumbers (expressed in ±2 cm$^{-1}$) of 636, 700, 847, 1054, 1203, 1263, 1298, 1336, 1410, 1521, 1550, 1572, 1605, 1663, 2941 and 3069 cm$^{-1}$. An FT Raman spectrum of a sample of form B is shown in FIG. 4. In a preferred embodiment, form B is characterized by an FT Raman spectrum substantially in accordance with FIG. 4.

Figure 5:
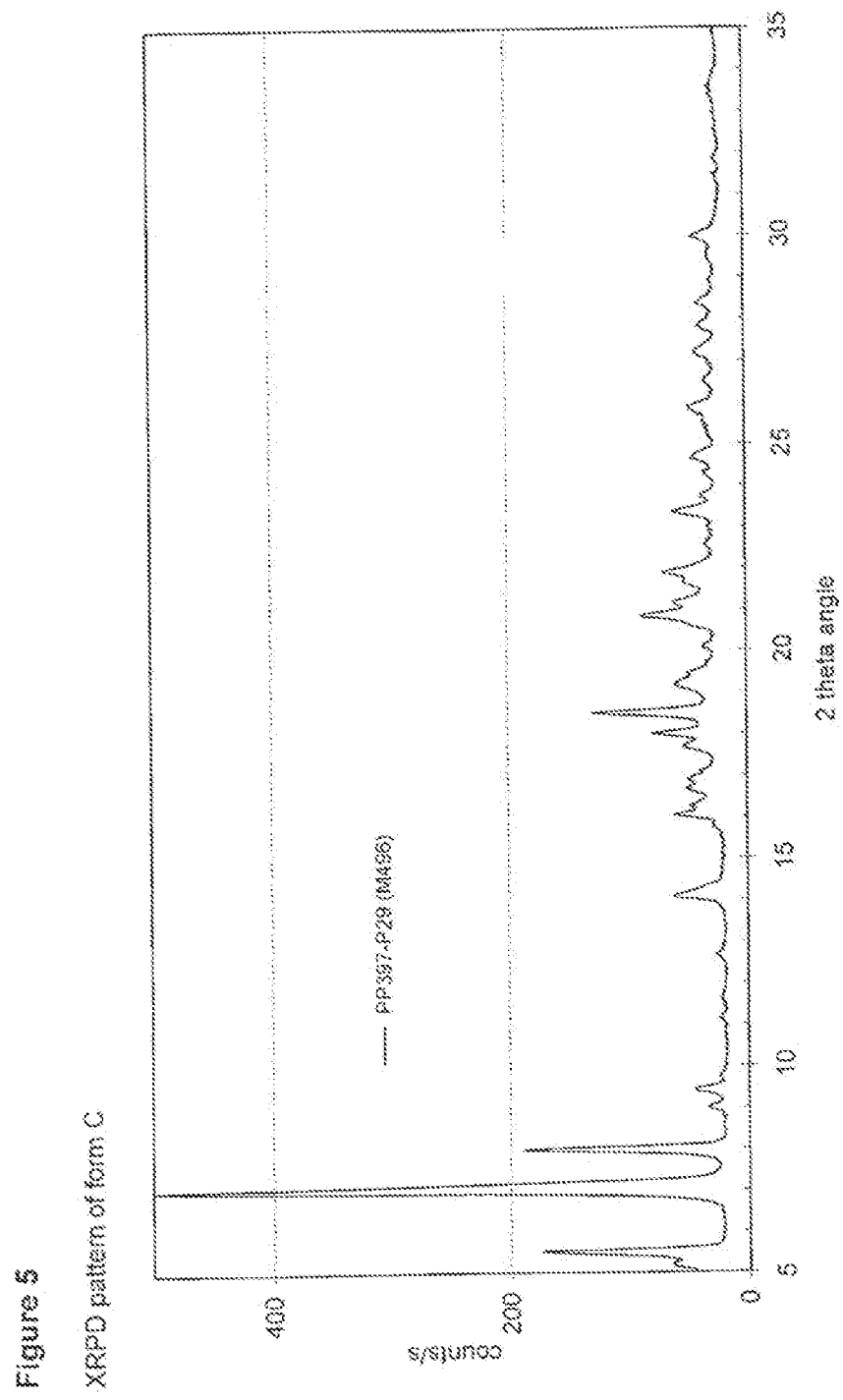

Preferably, the crystalline sodium salt has an XRPD pattern with at least one characteristic peak (expressed in 2θ±0.2° 2θ (CuKα radiation)) at 5.5°, 7.0°, 8.0° and 20.8°, designated as form C. Preferably, form C has an XRPD pattern with at least one characteristic peak (expressed in 2θ±0.2° 2θ (CuKα radiation)) at 5.5°, 7.0°. 8.0°, 18.0°, 18.5° and 20.8°. Typically such an X-ray powder diffractogram is measured with copper K-alpha radiation. An X-ray powder diffractogram of a sample of form C is shown in FIG. 5 and the present invention, in a preferred embodiment, relates to form C displaying a XRPD pattern which is substantially in accordance with FIG. 5.

Figure 6:
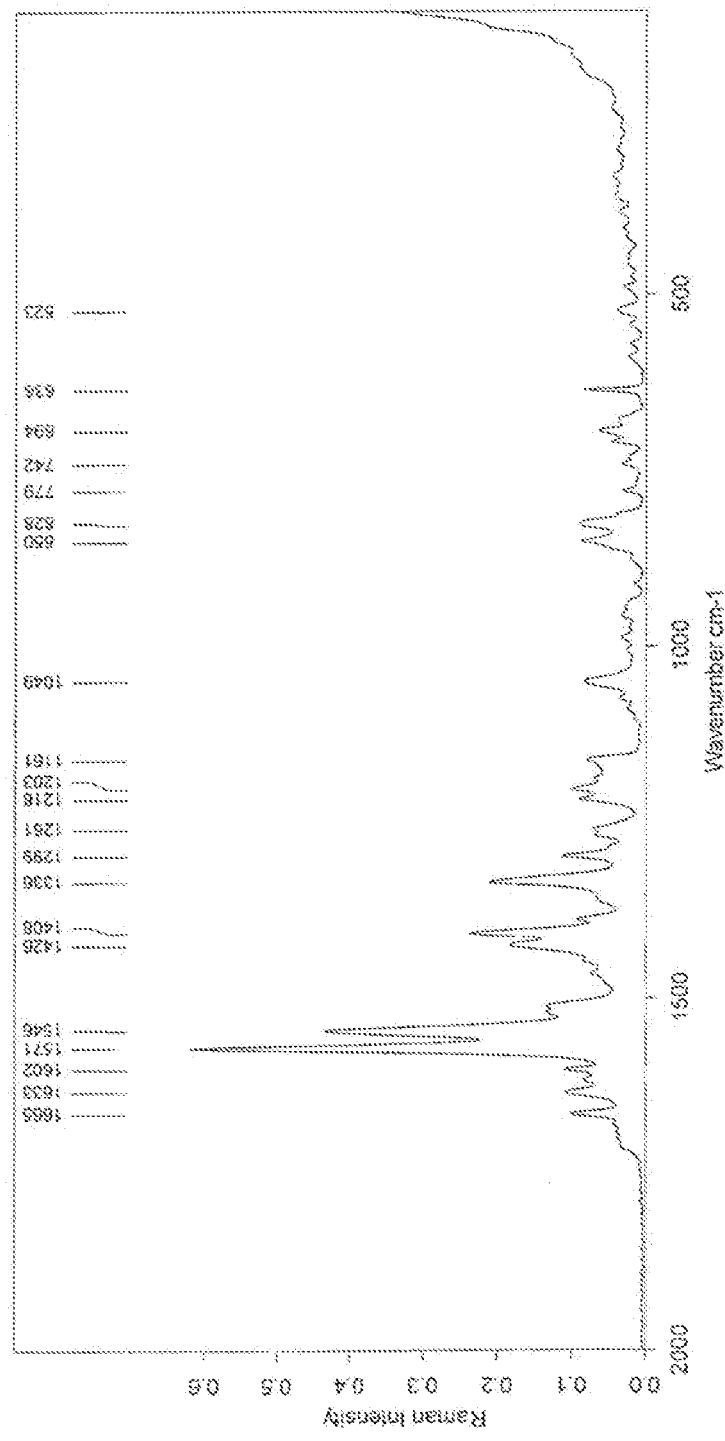

Preferably, form C has a FT-Raman spectrum comprising peaks at wavenumbers (expressed in ±2 cm$^{-1}$) of 636, 828, 1049, 1203, 1299, 1336, 1408, 1546, 1571, 2935, 3073 cm$^{-1}$. An FT Raman spectrum of a sample of form C is shown in FIG. 6. In a preferred embodiment, form C is characterized by an FT Raman spectrum substantially in accordance with FIG. 6.

Figure 7:
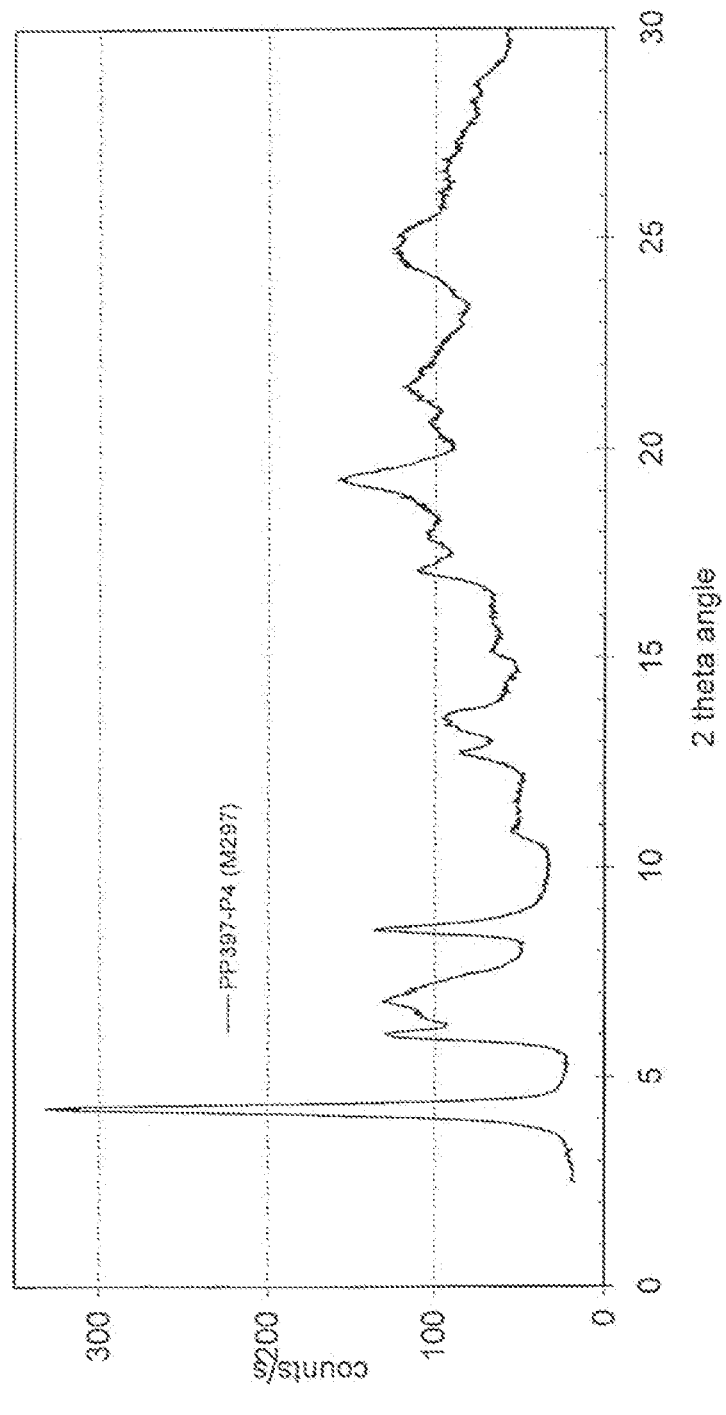

Preferably, the crystalline sodium salt has an XRPD pattern with at least one characteristic peak (expressed in 2θ±0.2° 2θ (CuKα radiation)) at 4.2°, 6.0°, 6.8°, 8.5° and 19.3°, designated as form D. Preferably, form D has it has an XRPD pattern with at least one characteristic peak (expressed in 2θ±0.2° 2θ (CuKα radiation)) at 4.2°, 6.0°, 6.8°, 8.5°, 12.7°, 13.5°, 17.0°, 17.9°, 19.3°, 21.5° and 24.7°. Typically such an X-ray powder diffractogram is measured with copper K-alpha radiation. An X-ray powder diffractogram of a sample of form D is shown in FIG. 7 and the present invention, in a preferred embodiment, relates to form D displaying a XRPD pattern which is substantially in accordance with FIG. 7.

Figure 8:
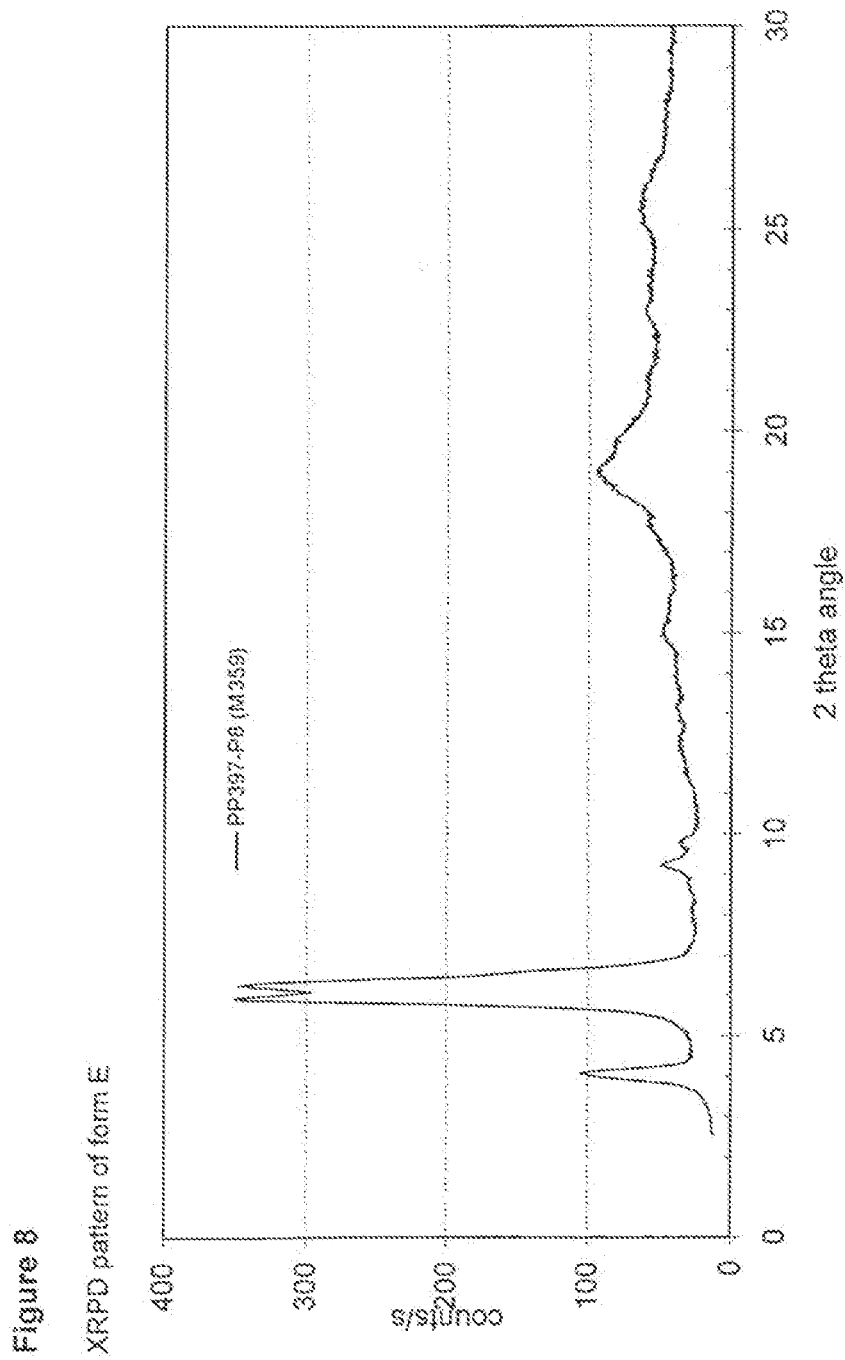

Preferably, the crystalline sodium salt has an XRPD pattern with at least one characteristic peak (expressed in 2θ±0.2° 2θ (CuKα radiation)) at 4.1°, 5.9°, 6.3° and 19.1°, designated as form E. Typically such an X-ray powder diffractogram is measured with copper K-alpha radiation. An X-ray powder diffractogram of a sample of form E is shown in FIG. 8 and the present invention, in a preferred embodiment, relates to form E displaying a XRPD pattern which is substantially in accordance with FIG. 8.

Figure 9:
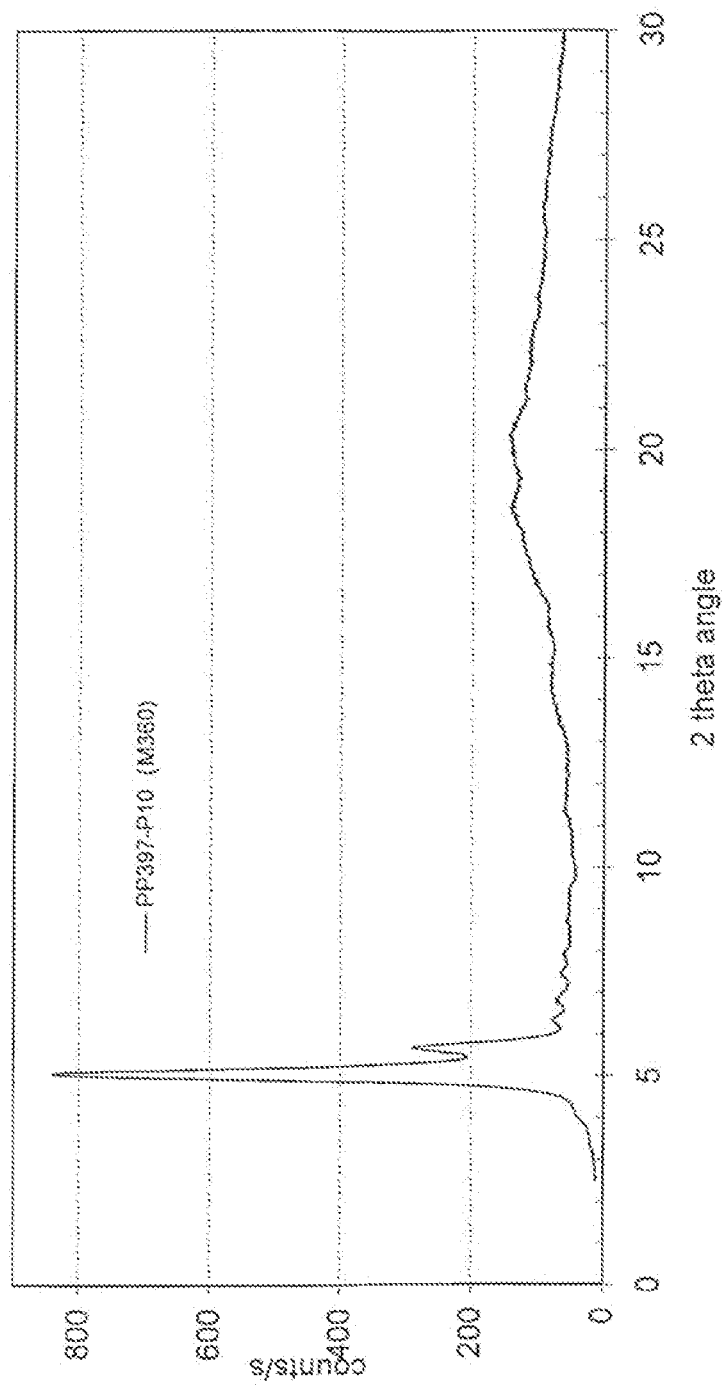

Preferably, the crystalline sodium salt has an XRPD pattern with at least one characteristic peak (expressed in 2θ±0.2° 2θ (CuKα radiation)) at 5.0°, 5.7°, 18.6° and 20.4°, designated as form F. Typically such an X-ray powder diffractogram is measured with copper K-alpha radiation. An X-ray powder diffractogram of a sample of form F is shown in FIG. 9 and the present invention, in a preferred embodiment, relates to form F displaying a XRPD pattern which is substantially in accordance with FIG. 9.

Figure 10:
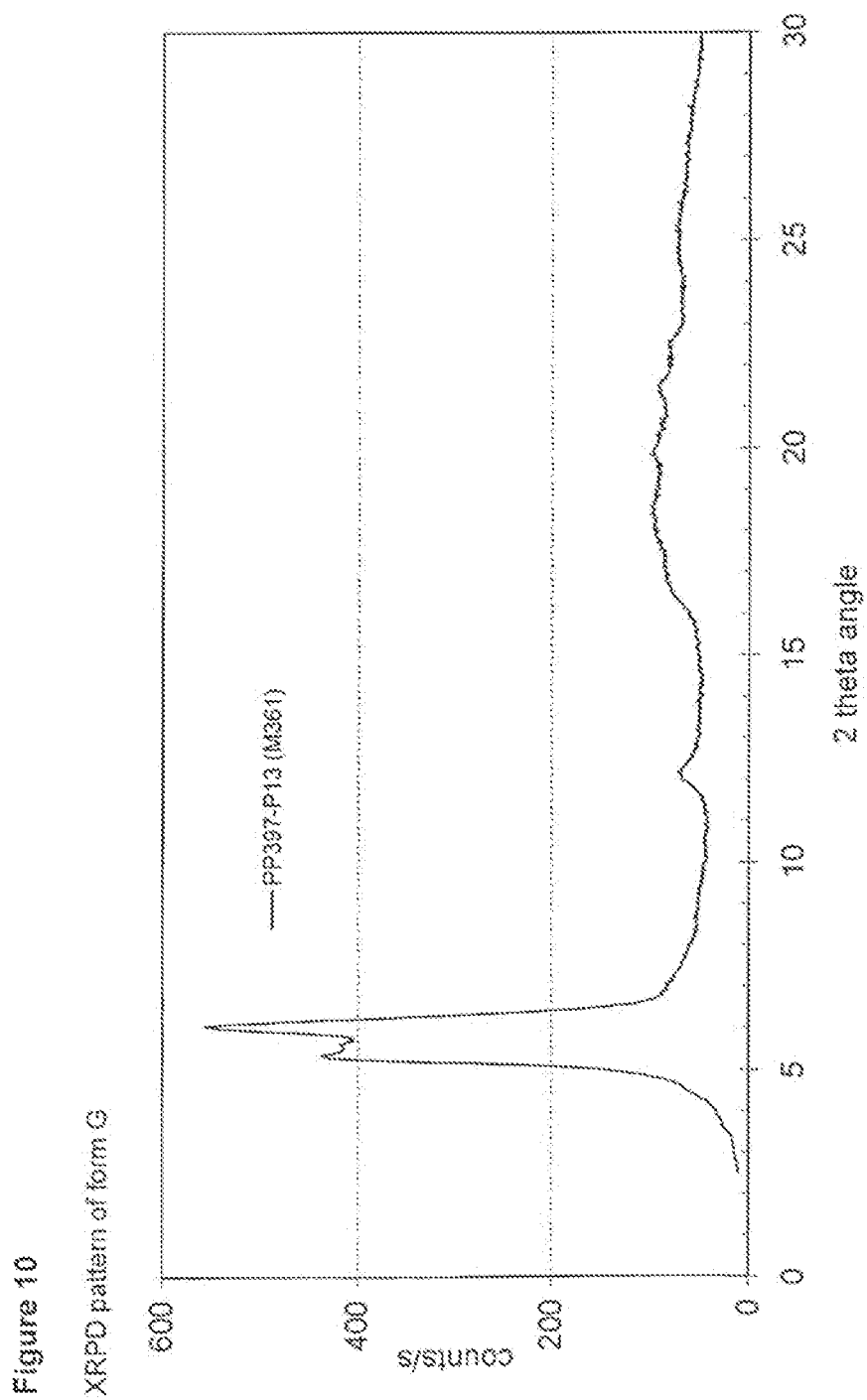

Preferably, the crystalline sodium salt has an XRPD pattern with at least one characteristic peak (expressed in 2θ±0.2° 2θ (CuKα radiation)) at 5.3°, 6.0° and 12.2°, designated as form G. Typically such an X-ray powder diffractogram is measured with copper K-alpha radiation. An X-ray powder diffractogram of a sample of form G is shown in FIG. 10 and the present invention, in a preferred embodiment, relates to form G displaying a XRPD pattern which is substantially in accordance with FIG. 10.

Preferably, the crystalline sodium salt has an XRPD pattern with at least one characteristic peak (expressed in 2θ±0.2° 2θ (CuKα radiation)) at 5.9°, 6.4°, 7.0° and 8.6°, designated as form H. Typically such an X-ray powder diffractogram is measured with copper K-alpha radiation. An X-ray powder diffractogram of a sample of form H is shown in FIG. 11 and the present invention, in a preferred embodiment, relates to form H displaying a XRPD pattern which is substantially in accordance with FIG. 11.

A further aspect of the present invention is a process for obtaining the crystalline sodium salts of the present invention comprising the steps of:
a) providing a compound of formula I (INN: Raltegravir)

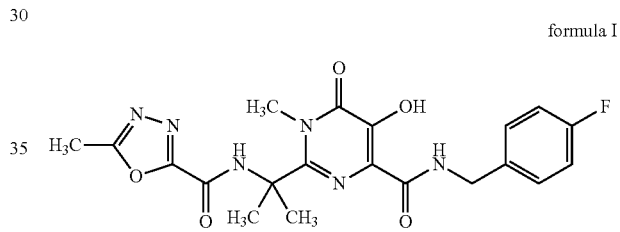

formula I in a suitable solvent or a mixture of solvents;
b) adding an aqueous solution comprising sodium hydroxide to the mixture of step a);
c) optionally concentrating the composition of step b);
d) crystallizing;
e) optionally equilibrating the obtained suspension of step d); and
f) isolating the obtained precipitate.

Preferably, the molar ratio of the compound of formula I in step a) and the sodium hydroxide of step b) is in the range of from 1:0.5 to 1:1.2 and even more preferred is 1:1.

Alternatively, the crystalline compounds of the present invention can be obtained by a process comprising the steps of:
a) providing a sodium salt of a compound of formula I (INN: Raltegravir)

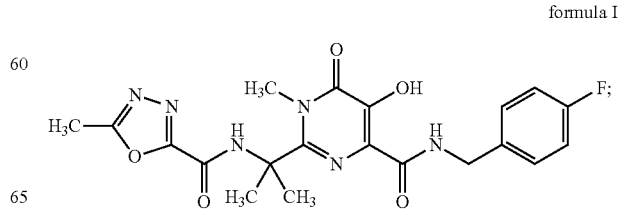

formula I b) adding a suitable solvent or mixture of solvents to the compound of step a);
c) optionally concentrating the composition of step b);
d) crystallizing;
e) optionally equilibrating the obtained suspension of step d); and
f) isolating the obtained precipitate.

For both alternative processes, preferably in step c) the solvent is removed and the residue is dissolved in a suitable solvent or mixture of solvents and water.

Preferably, the solvent is selected from the group consisting of C2-C4 alcohols, a C3-C6 ketone, an ether or an acetic ester, C1-C4 alkylester, acetonitrile, a hydrocarbon or mixtures thereof.

In a further preferred embodiment, in step d) seed crystals are added.

Preferably, for obtaining form A of the present invention acetonitrile is used as solvent in step a). In step b) preferably an aqueous sodium hydroxide solution is added to the composition of step a), whereby the molar ratio of the compound of formula I in step a) and the sodium hydroxide of step b) is 1:1. Surprisingly, form A can be obtained in high yield with an accurate process having low complexity.

The present invention also relates to a pharmaceutical composition comprising the aforementioned crystalline sodium salt and optionally one or more pharmaceutically acceptable excipients.

A further aspect of the present invention is the aforementioned crystalline sodium salt for use in the treatment of or in the prevention of an infection by HIV and/or for use in the treatment of, in the prevention of or in the delay of the onset of AIDS in a subject in need thereof.

EXAMPLES

Raman Spectroscopy

FT-Raman spectroscopy was performed using a Bruker RFS100 (Nd:YAG 1064 nm exitation, 300 mW laser power, Ge detector, 64 scans, range 25 3500 cm$^{-1}$, 2 cm$^{-1}$ resolution)

DSC

Differential scanning calorimetry is a well known method in the art that measures the heat flow through a sample upon heating at a defined rate. It is a suitable method to determine the melting temperatures, the glass transition temperature, or other thermal events such as phase conversions or thermal decomposition.

DSC was performed using a Perkin Elmer DSC 7. Measurements were performed in closed Au crucibles, at heating rates or 10 or 20° C. min$^{-1}$, range 50° C. to 250° C.

XRPD

The measurements were carried out with a Bruker D8 Advance powder X-ray diffractometer using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The samples were prepared without any special treatment other than the application of slight pressure to get a flat surface. Silicon single crystal sample holders of either 0.5 mm or 0.1 mm depth and 12 mm cavity diameter were used. The tube voltage and current were 40 kV and 40 mA, respectively. The X-ray diffractometer is equipped with a LynxEye detector. A variable divergence slight was used with a 3° window. The step size was 0.02° 2θ with a step time of 37 seconds. The samples were rotated at 0.5 rps during the measurement.

TG-FTIR

Thermogravimetry coupled with FT-infrared spectroscopy is a well known method that allows to monitor the mass loss of a given sample upon heating while identifying the volatile substances by infrared spectroscopy. Therefore, TG-FTIR is a suitable method to identify solvates or hydrates.

TG-FTIR was performed on a Netzsch Thermo-Microbalance TG 209, which is coupled to a Bruker FT-IR Spectrometer Vector 22. The measurements were carried out with aluminum crucibles with a micro pinhole under a nitrogen atmosphere and at a heating rate of 10° C./min over the range 25-250° C.

Example 1

Preparation of Form A 100 mg raltegravir free acid (compound of formula 1) (~0.22 mmol) is dissolved in 0.5 ml acetonitrile at 75° C. One equivalent of sodium hydroxide is added in form of a 6M aqueous solution (37.6 µl) and the solution is slowly cooled to room temperature. At room temperature further 0.5 ml acetonitrile is added and stirring is continued for about 18 hours. The resulting suspension is filtered off and the crystalline product is first dried at room temperature under vacuum then for two hours at 200° C., thereafter investigated by powder X-ray diffraction, H-NMR, elemental composition analysis, DSC and TG-FTIR. The structural integrity of the compound is confirmed by H-NMR spectroscopy. The sodium content is verified by elemental analysis. The result of the elemental composition analysis is depicted in table 1. Both methods provide the supporting evidence for the formation of the sodium salt. The obtained XRPD pattern as depicted in FIG. 1 with the most important peaks as provided in table 2 shows that the obtained salt is crystalline. TG-FTIR reveals a mass loss of about 1.4% which is attributable to water. DSC shows a melting peak at 256° C. which is followed by thermal decomposition. The Raman spectrum of form A is shown in FIG. 2 and the corresponding list with the band locations is provided in table 3.

TABLE 1

Elemental composition result for form A.

| Element | Measured Values (mass %) |
| --- | --- |
| C | 50.6% |
| H | 4.2% |
| N | 18.0% |
| O | 18.6% |
| Na | 4.8% |
| $H_2O$ | 1.4 wt-% (TG-FTIR) |

TABLE 2

Most important powder X-ray diffraction peaks for form A (M673)

| Pos. [°2θ] | d-spacing [Å] | Qualitative Intentsity |
| --- | --- | --- |
| 5.7 | 15.6 | m |
| 7.3 | 12.2 | vs |
| 8.0 | 11.0 | s |
| 11.3 | 7.8 | w |

TABLE 2-continued

Most important powder X-ray diffraction peaks for form A (M673)

| Pos. [°2θ.] | d-spacing [Å] | Qualitative Intentsity |
|---|---|---|
| 11.8 | 7.5 | w |
| 12.7 | 7.0 | w |
| 13.1 | 6.7 | w |
| 14.2 | 6.2 | w |
| 14.4 | 6.2 | w |
| 14.9 | 5.94 | w |
| 16.0 | 5.53 | w |
| 16.4 | 5.40 | w |
| 16.7 | 5.31 | m |
| 16.9 | 5.24 | w |
| 17.5 | 5.07 | w |
| 18.0 | 4.93 | s |
| 18.6 | 4.77 | m |
| 19.4 | 4.58 | m |
| 20.7 | 4.30 | w |
| 21.1 | 4.21 | m |
| 21.8 | 4.08 | s |
| 22.2 | 4.00 | w |
| 22.8 | 3.89 | w |
| 23.5 | 3.79 | m |
| 24.3 | 3.66 | m |
| 24.9 | 3.57 | m |
| 25.4 | 3.50 | m |
| 25.8 | 3.45 | w |
| 26.2 | 3.40 | m |
| 26.9 | 3.31 | w |
| 27.3 | 3.26 | w | vs: very strong, s: strong, m: medium, w: weak, vw: very weak intensity

TABLE 3

Most important Raman bands of form A (P40)

| wavenumbers [cm$^{-1}$] | Qualitative relative Intensity |
|---|---|
| 3073 | m |
| 3004 | vw |
| 2937 | m |
| 1690 | w |
| 1664 | w |
| 1630 | w |
| 1614 | vw |
| 1570 | vs |
| 1550 | s |
| 1425 | vw |
| 1410 | m |
| 1389 | vw |
| 1335 | m |
| 1298 | w |
| 1261 | w |
| 1218 | w |
| 1201 | vw |
| 1171 | vw |
| 1158 | vw |
| 1051 | w |
| 988 | vw |
| 850 | m |
| 831 | vw |
| 781 | vw |
| 741 | vw |
| 703 | vw |
| 692 | w |
| 676 | vw |
| 637 | w |
| 588 | vw |
| 525 | w |
| 329 | w |

Example 2

Preparation of Form A 36 mg raltegravir sodium salt form D is suspended in 0.5 ml ethanol containing 5% water (by volume, ethanol-water 95:5) and shaken at 450 rpm under temperature cycling ($T_1$=25° C., $T_2$=30° C. with a holding time of one hour, heating and cooling rate 5° C. per hour). After three days of shaking the temperature cycling program is adjusted as follows: $T_1$=25° C., $T_2$=40° C. with a holding time of one hour, heating and cooling rate 15° C. per hour. After 14 days the suspension is filtered and the obtained solid is investigated by FT-Raman it spectroscopy. The FT-Raman spectrum is in accordance with FIG. 2 and corresponds to form A.

Example 3

Preparation of Form A 800 mg raltegravir free base is dissolved in 4 ml acetonitrile at 75° C. One equivalent of sodium hydroxide is added in form of a 6 molar aqueous solution. Then a few mg of seed crystals as obtained in example 1 is added and the obtained suspension was cooled to r.t. At 60° C. additional 25 ml of acetonitrile is added to dilute the resulting rather thick suspension. After cooling to room temperature and stirring for one hour the suspension is filtered and the solid dried under vacuum at room temperature. A yield of about 720 mg is obtained. The crystalline solid is investigated by powder X-ray diffraction and the obtained XRPD pattern is attributable to raltegravir sodium salt form A as shown in FIG. 1.

Example 4

Solubility and Stability of Form a in Water (P70)

104 mg of raltegravir sodium salt form A is suspended in 1.0 ml water and the suspension placed on a laboratory shaker at 22±2° C. for 24 hours at a rate of 400 rpm. After 24 hours shaking the suspension is filtered, the obtained solid investigated by powder X-ray diffraction, and the concentration in the liquid phase is determined by UV-vis spectroscopy. XRPD shows that the crystalline form A is retained and the aqueous solubility at a resulting pH of 10.4 was found to be 47±5 mg/ml.

Example 5

Preparation of Form B 50 mg raltegravir free acid is dissolved in 4.5 ml ethanol at 75° C. One equivalent of sodium hydroxide is added in form of a 6M aqueous solution (18.8 μl) and the solution is stirred at 75° C. for about three hours, and then cooled to 25° C. with a cooling rate of 5° C. per hour. Stirring is continued for about two days at 25° C. and a slightly turbid solution is obtained. After sonicating the turbid solution is concentrated to about 2 ml, shortly heated with a heat gun and then again stirred at room temperature. As the sample revealed no changes after four days it was stored at r.t. without stirring, but after one additional day crystals were formed. The suspension was filtered, the solid was dried under vacuum at room temperature, and investigated by FT-Raman spectroscopy, powder X-ray diffraction, TG-FTIR, DSC, and H-NMR. The structural integrity of the compound is confirmed by H-NMR. Analysis of the sodium content by atomic absorption spectroscopy shows the presence of 4.8% (w/w) sodium which is consistent with a molar ratio of Raltegravir and sodium of about 1:1. TG-FTIR indicates a mass loss of about 2.5% which is attributable to water and ethanol. The XRPD pattern as shown in FIG. 3 corresponds to raltegravir form B for which the most important peaks are provided in table 4. The Raman spectrum of form B is shown in FIG. 4 and the corresponding list with the band locations is provided in table 5.

TABLE 4

Most important powder X-ray diffraction peaks for form (M437, P29-10)

| Pos. [°2θ.] | d-spacing [Å] | Qualitative Intentsity |
|---|---|---|
| 5.7 | 15.5 | m |
| 7.0 | 12.6 | vs |
| 7.7 | 11.4 | m |
| 11.1 | 8.0 | vw |
| 11.3 | 7.8 | vw |
| 11.7 | 7.6 | vw |
| 13.6 | 6.5 | w |
| 14.9 | 5.95 | vw |
| 15.4 | 5.74 | w |
| 16.7 | 5.29 | vw |
| 17.9 | 4.96 | w |
| 18.8 | 4.71 | w |
| 19.3 | 4.60 | w |
| 20.1 | 4.40 | w |
| 20.9 | 4.25 | w |
| 21.7 | 4.09 | w |
| 22.8 | 3.90 | vw |
| 23.4 | 3.80 | w |
| 24.0 | 3.71 | vw |
| 25.1 | 3.55 | w |
| 25.4 | 3.50 | w |
| 26.1 | 3.41 | w |
| 26.8 | 3.32 | w |
| 27.4 | 3.26 | vw |
| 28.4 | 3.14 | vw |

TABLE 5

Most important Raman bands of form B (P29-1)

| wavenumbers [cm$^{-1}$] | Qualitative relative Intensity |
|---|---|
| 3069 | w |
| 2941 | m |
| 1689 | vw |
| 1663 | w |
| 1605 | w |
| 1572 | vs |
| 1550 | s |
| 1521 | w |
| 1410 | m |
| 1389 | vw |
| 1336 | m |
| 1298 | w |
| 1263 | w |
| 1203 | w |
| 1054 | w |
| 847 | m |
| 700 | w |
| 636 | w |
| 522 | vw |
| 333 | vw |

Example 6

Formation of Form C by Treatment of Form B at 200° C. (P29-2)

20 mg raltegravir sodium salt form B according to example 5 are heated to 200° C. and kept at this temperature for 30 minutes. Thereafter, powder X-ray diffraction and Raman spectroscopy is performed. An XRPD pattern as shown in FIG. 5 is found for the temperature treated form B and this XRPD pattern is designated to form C. The peak list is shown in table 6. The Raman spectrum of form C is shown in FIG. 6 and the corresponding list with the band locations is provided in table 7.

TABLE 6

Powder X-ray diffraction peaks for form C (M496, P29-2)

| Pos. [°2θ.] | d-spacing [Å] | Qualitative Intentsity |
|---|---|---|
| 5.2 | 17.0 | w |
| 5.5 | 16.1 | s |
| 7.0 | 12.6 | vs |
| 8.0 | 11.1 | s |
| 9.0 | 9.8 | vw |
| 9.4 | 9.4 | w |
| 14.1 | 6.3 | w |
| 16.1 | 5.51 | w |
| 16.8 | 5.28 | w |
| 17.7 | 5.01 | w |
| 18.0 | 4.92 | m |
| 18.5 | 4.80 | m |
| 19.2 | 4.62 | w |
| 20.8 | 4.26 | s |
| 21.2 | 4.20 | w |
| 21.9 | 4.06 | w |
| 23.3 | 3.81 | w |
| 24.7 | 3.61 | vw |
| 25.9 | 3.44 | vw |
| 27.2 | 3.28 | vw |
| 27.8 | 3.21 | vw |
| 28.4 | 3.15 | vw |
| 30.0 | 2.98 | vw |

TABLE 7

Raman bands of form C (P29-2)

| wavenumbers [cm$^{-1}$] | Qualitative relative Intensity |
|---|---|
| 3073 | w |
| 2996 | vw |
| 2935 | m |
| 1665 | vw |
| 1633 | vw |
| 1602 | vw |
| 1571 | vs |
| 1546 | m |
| 1426 | vw |
| 1408 | m |
| 1336 | m |
| 1299 | w |
| 1261 | vw |
| 1203 | w |
| 1049 | w |
| 850 | vw |
| 828 | w |
| 694 | vw |
| 636 | w |

Example 7

Preparation of Form D (P4)

1.0 g raltegravir free acid is dissolved in 20 ml acetonitrile and one equivalent of sodium hydroxide is added in form of a 6 molar aqueous solution (375 μl). The mixture is stirred at r.t. and after about 2 hours a suspension is formed which is further stirred for about one day at r.t. The suspension is filtered and the solid dried under vacuum at r.t. Investigation by powder X-ray diffraction shows that crystalline sodium salt is obtained. The structural integrity of the compound is confirmed by H-NMR spectroscopy. Elemental composition analysis, as shown in table 8, is consistent with a raltegravir sodium salt with molar ratio of raltegravir to sodium of 1:1. TG-FTIR reveals a mass loss of about 2.8% which is attributable to water. DSC shows a melting peak at 191° C. The PXRD pattern of the obtained form, designated as form D, is shown in FIG. 7 and a list of X-ray diffraction peaks is provided in table 9.

TABLE 8

Elemental composition result for form D

| Element | Measured Values (mass %) |
| --- | --- |
| C | 50.1% |
| H | 4.6% |
| N | 17.7% |
| O | 18.6% |
| F | 4.0% |
| Na | 4.9% |
| $H_2O$ | 2.77% (TG-FTIR) |

TABLE 9

Powder X-ray diffraction peaks for form D (M297, P4)

| Pos. [°2θ.] | d-spacing [Å] | Qualitative Intentsity |
| --- | --- | --- |
| 4.2 | 20.8 | vs |
| 6.0 | 14.7 | m |
| 6.8 | 12.9 | m |
| 8.5 | 10.4 | m |
| 12.7 | 7.0 | w |
| 13.5 | 6.6 | w |
| 15.2 | 5.84 | vw |
| 17.0 | 5.20 | w |
| 17.9 | 4.96 | w |
| 19.3 | 4.59 | m |
| 21.5 | 4.14 | w |
| 24.7 | 3.60 | w |
| 28.8 | 3.10 | vw |

Example 8

Preparation of Form E (P8)

35 mg raltegravir sodium salt form D is suspended in 0.5 ml methyl ethyl ketone (MEK) and the mixture is shaken at a rate of 450 rpm under temperature cycling ($T_1=25°$ C., $T_2=30°$ C. with a holding time of one hour, heating and cooling rate 5° C./h). After three days 0.25 ml MEK is added and the suspension shaking continued for two days with the same temperature cycling. Then the suspension is filtered and the solid product dried under vacuum for one hour. Investigation by powder X-ray diffraction shows that a new form is obtained. This form is designated as form E, with a powder X-ray diffraction pattern as shown in FIG. 8 and diffraction peaks as listed in table 10. Analysis of the sodium content by atomic absorption spectroscopy shows the presence of 4.9% (w/w) sodium which is consistent with a molar ratio of Raltegravir and sodium of about 1:1.

TABLE 10

Powder X-ray diffraction peaks for form E (M359, P8)

| Pos. [°2θ.] | d-spacing [Å] | Qualitative Intentsity |
| --- | --- | --- |
| 4.1 | 21.8 | m |
| 5.9 | 15.0 | vs |
| 6.3 | 14.1 | vs |
| 9.3 | 9.5 | vw |
| 9.8 | 9.0 | vw |
| 15.0 | 5.89 | vw |
| 19.1 | 4.64 | w |
| 22.9 | 3.88 | vw |

Example 9

Preparation of Form F (P10)

35 mg raltegravir sodium salt form D is dissolved in 0.5 ml of a mixture of THF.ethyl acetate 1:3 (v/v) and shaken at a rate of 450 rpm under temperature cycling ($T_1=25°$ C., $T_2=30°$ C. with a holding time of 1 h, heating and cooling rate 5° C./h). After three days 0.25 mL of additional solvent mixture is added and shaking continued for two days with the same temperature cycling program. Then the suspension is filtered and the solid product dried under vacuum for one hour. Investigation by powder X-ray diffraction shows that a new form is obtained. This form is designated as form F, with a powder X-ray diffraction pattern as shown in FIG. 9 and diffraction peaks as listed in table 11. Analysis of the sodium content by atomic absorption spectroscopy shows the presence of 5.0% (w/w) sodium which is consistent with a molar ratio of Raltegravir and sodium of about 1:1.

TABLE 11

Powder X-ray diffraction peaks for form F (M360, P10)

| Pos. [°2θ.] | d-spacing [Å] | Qualitative Intentsity |
| --- | --- | --- |
| 5.0 | 17.5 | vs |
| 5.7 | 15.6 | m |
| 6.4 | 13.9 | vw |
| 7.0 | 12.6 | vw |
| 7.4 | 11.9 | vw |
| 14.2 | 6.2 | vw |
| 18.6 | 4.77 | w |
| 20.4 | 4.38 | w |

Example 10

Preparation of Form G (P13)

35 mg raltegravir sodium salt form D is suspended in 0.5 ml of a mixture with 1,4-dioxane and cyclohexane 3:1 (v/v) and shaken at a rate of 450 rpm under temperature cycling with the following program: $T_1=25°$ C., $T_2=30°$ C. with a holding time of one hour, heating and cooling rate 5° C. per hour. After five days the suspension is filtered and the solid product dried under vacuum for one hour. Investigation by powder X-ray diffraction shows that a new form is obtained. This form is designated as form G, with a powder X-ray diffraction pattern as shown in FIG. 10 and diffraction peaks as listed in table 12. Analysis of the sodium content by atomic absorption spectroscopy shows the presence of 4.6% (w/w) sodium which is consistent with a molar ratio of Raltegravir and sodium of about 1:1.

TABLE 12

Powder X-ray diffraction peaks for form G (M361, P13)

| Pos. [°2θ.] | d-spacing [Å] | Qualitative Intentsity |
|---|---|---|
| 5.3 | 16.4 | vs |
| 6.0 | 14.6 | vs |
| 12.2 | 7.3 | vw |
| 16.9 | 5.3 | vw |
| 18.2 | 4.9 | vw |
| 19.6 | 4.5 | vw |
| 21.6 | 4.1 | vw |

Example 11

Preparation of Form H (P18)

35 mg raltegravir sodium salt form D is suspended in 0.5 ml of a mixture with THF/H$_2$O 95:5 (v/v) and shaken at a rate of 450 rpm under temperature cycling with the following program: T$_1$=25° C., T$_2$=30° C. with a holding time of one hour, heating and cooling rate 5° C. per hour. After five days the suspension is filtered and the solid product dried under vacuum for one hour. Investigation by powder X-ray diffraction shows that a new form is obtained. This form is designated as form H, with a powder X-ray diffraction pattern as shown FIG. 11 and diffraction peaks as listed in table 13. Analysis of the sodium content by atomic absorption spectroscopy shows the presence of 4.8% (w/w) sodium which is consistent with a molar ratio of Raltegravir and sodium of about 1:1.

TABLE 13

Powder X-ray diffraction peaks for form H (M362, P18)

| Pos. [°2θ.] | d-spacing [Å] | Qualitative Intentsity |
|---|---|---|
| 5.9 | 14.9 | s |
| 6.4 | 13.7 | vs |
| 7.0 | 12.5 | s |
| 8.6 | 10.3 | m |
| 13.2 | 6.7 | vw |
| 14.0 | 6.3 | vw |
| 16.7 | 5.3 | vw |
| 17.5 | 5.1 | vw |
| 18.9 | 4.7 | vw |
| 19.5 | 4.5 | vw |
| 21.6 | 4.1 | vw |
| 22.7 | 3.9 | vw |
| 24.0 | 3.7 | vw |
| 24.6 | 3.6 | vw |
| 26.0 | 3.4 | vw |
| 28.3 | 3.2 | vw |

The invention claimed is:

1. A crystalline sodium salt of a compound of formula I (INN: Raltegravir)

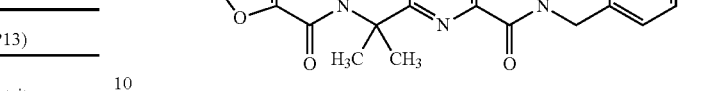

formula I or a hydrate/solvate thereof.

2. The crystalline compound of claim 1, characterized in that the molar ratio of the compound of formula I and sodium is in the range of from 1:0.5 to 1:1.

3. The crystalline compound of claim 1, characterized in that it has an XRPD pattern with at least one characteristic peak (expressed in 2θ±0.2° 2θ (CuKα radiation)) at 5.7°, 7.3°, 8.0°, 18.0° and 21.8°, designated as form A.

4. The crystalline compound of claim 3, characterized in that it has an XRPD pattern with at least one characteristic peak (expressed in 2θ±0.2° 2θθ (CuKα radiation)) at 5.7°, 7.3°, 8.0°, 11.8°, 16.7°, 18.0°, 18.6°, 19.4°, 21.1° and 21.8°.

5. The crystalline compound according to claim 3, characterized in that it has a FT-Raman spectrum comprising peaks at wavenumbers (expressed in ±2 cm$^{-1}$) of 637, 692, 850, 1051, 1218, 1261, 1298, 1335, 1410, 1550, 1570, 1630, 1664, 1690, 2937 and 3073 cm$^{-1}$.

6. The crystalline compound of claim 1, characterized in that it has an XRPD pattern with at least one characteristic peak (expressed in 2θ±0.2° 2θ (CuKα radiation)) at 5.7°, 7.0° and 20.9°, designated as form B.

7. The crystalline compound of claim 6, characterized in that it has an XRPD pattern with at least one characteristic peak (expressed in 2θ±0.2° 2θ (CuKα radiation)) at 5.7°, 7.0°, 7.7°, 15.4°, 17.9°, 20.9° and 21.7°.

8. The crystalline compound according to claim 6, characterized in that it has a FT-Raman spectrum comprising peaks at wavenumbers (expressed in ±2 cm$^{-1}$) of 636, 700, 847, 1054, 1203, 1263, 1298, 1336, 1410, 1521, 1550, 1572, 1605, 1663, 2941 and 3069 cm$^{-1}$.

9. The crystalline compound of claim 1, characterized in that it has an XRPD pattern with at least one characteristic peak (expressed in 2θ±0.2° 2θ (CuKα radiation)) at 5.5°, 7.0°, 8.0° and 20.8°, designated as form C.

10. The crystalline compound of claim 9, characterized in that it has an XRPD pattern with at least one characteristic peak (expressed in 2θ±0.2° 2θ (CuKα radiation)) at 5.5°, 7.0°, 8.0°, 18.0°, 18.5° and 20.8°.

11. The crystalline compound according to claim 9, characterized in that it has a FT-Raman spectrum comprising peaks at wavenumbers (expressed in ±2 cm$^{-1}$) of 636, 828, 1049, 1203, 1299, 1336, 1408, 1546, 1571, 2935, 3073 cm$^{-1}$.

12. The crystalline compound of claim 1, characterized in that it has an XRPD pattern with at least one characteristic peak (expressed in 2θ±0.2° 2θ (CuKα radiation)) at 4.2°, 6.0°, 6.8°, 8.5° and 19.3°, designated as form D.

13. The crystalline compound of claim 12, characterized in that it has an XRPD pattern with at least one characteristic peak (expressed in 2θ±0.2° 2θ (CuKα radiation)) at 4.2°, 6.0°, 6.8°, 8.5°, 12.7°, 13.5°, 17.0°, 17.9°, 19.3°, 21.5° and 24.7°.

14. The crystalline compound of claim 1, characterized in that it has an XRPD pattern with at least one characteristic peak (expressed in 2θ±0.2° 2θ (CuKα radiation)) at 4.1°, 5.9°, 6.3° and 19.1°, designated as form E.

15. The crystalline compound of claim 1, characterized in that it has an XRPD pattern with at least one characteristic peak (expressed in 2θ±0.2° 2θ (CuKα radiation)) at 5.0°, 5.7°, 18.6° and 20.4°, designated as form F.

16. The crystalline compound of claim 1, characterized in that it has an XRPD pattern with at least one characteristic peak (expressed in 2θ±0.2° 2θ (CuKα radiation)) at 5.3°, 6.0° and 12.2°, designated as form G.

17. The crystalline compound of claim 1, characterized in that it has an XRPD pattern with at least one characteristic peak (expressed in 2θ±0.2° 2θ (CuKα radiation)) at 5.9°, 6.4°, 7.0° and 8.6°, designated as form H.

18. A process for obtaining the crystalline compound according to claim 1 comprising the steps of:
    a) providing a compound of formula I (INN: Raltegravir)

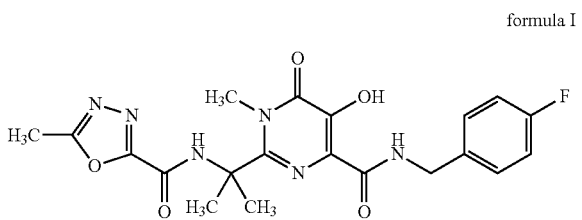 [SMILES: Cc1nnc(C(=O)NC(C)(C)c2nc(C(=O)NCc3ccc(F)cc3)c(O)c(=O)n2C)o1]

formula I in a suitable solvent or a mixture of solvents;
    b) adding an aqueous solution comprising sodium hydroxide to the mixture of step a);
    c) optionally concentrating the composition of step b);
    d) crystallizing;
    e) optionally equilibrating the obtained suspension of step d); and
    f) isolating the obtained precipitate.

19. The process of claim 18, characterized in that the molar ratio of the compound of formula I in step a) and the sodium hydroxide of step b) is in the range of from 1:0.5 to 1:1.2.

20. A process for obtaining a crystalline compound according to claim 1 comprising the steps of:
    a) providing a sodium salt of a compound of formula I (INN: Raltegravir)

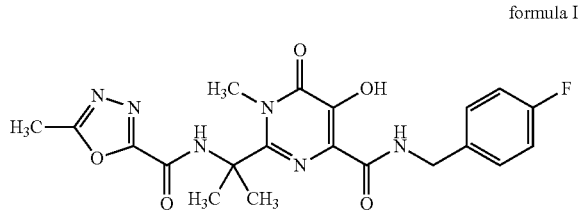 [SMILES: Cc1nnc(C(=O)NC(C)(C)c2nc(C(=O)NCc3ccc(F)cc3)c(O)c(=O)n2C)o1]

formula I b) adding a suitable solvent or mixture of solvents to the compound of step a);
    c) optionally concentrating the composition of step b);
    d) crystallizing;
    e) optionally equilibrating the obtained suspension of step d); and
    f) isolating the obtained precipitate.

21. The process of claim 18, characterized in that in step c) the solvent is removed and the residue is dissolved in a suitable solvent or mixture of solvents and water.

22. The process of claim 18, characterized in that the solvent is selected from the group consisting of C2-C4 alcohols, a C3-C6 ketone, an ether or an acetic ester, C1-C4 alkylester, acetonitrile, a hydrocarbon and mixtures thereof.

23. The process of claim 18, characterized in that in step d) seed crystals are added.

24. A pharmaceutical composition comprising the crystalline compound according to claim 1 and optionally one or more pharmaceutically acceptable excipients.

25. A method for the treatment or prevention of an infection by HIV and/or the treatment or prevention or delay of the onset of AIDS, the method comprising administering to a subject in need thereof an effective amount of the crystalline compound of claim 1.

\* \* \* \* \*

UNITED STATES PATENT AND TRADEMARK OFFICE
CERTIFICATE OF CORRECTION

PATENT NO. : 9,458,146 B2
APPLICATION NO. : 14/115316
DATED : October 4, 2016
INVENTOR(S) : F. Blatter et al.

It is certified that error appears in the above-identified patent and that said Letters Patent is hereby corrected as shown below:

On the Title Page

Item (75), first inventor should read:
Fritz Blatter, Reinach (CH)

Signed and Sealed this
Thirtieth Day of October, 2018

Andrei Iancu
*Director of the United States Patent and Trademark Office*